US012440662B2

(12) United States Patent
Sanikommu

(10) Patent No.: US 12,440,662 B2
(45) Date of Patent: Oct. 14, 2025

(54) STABLE FLOW REGULATOR ASSEMBLY

(71) Applicant: Carefusion 303, Inc., San Diego, CA (US)

(72) Inventor: Narsireddy Sanikommu, Kothapeta Kanigiri (IN)

(73) Assignee: CAREFUSION 303, INC., San Diego, CA (US)

( * ) Notice: Subject to any disclaimer, the term of this patent is extended or adjusted under 35 U.S.C. 154(b) by 584 days.

(21) Appl. No.: 17/901,381

(22) Filed: Sep. 1, 2022

(65) Prior Publication Data

US 2024/0075207 A1 Mar. 7, 2024

(51) Int. Cl.
*A61M 39/28* (2006.01)
*A61M 5/168* (2006.01)

(52) U.S. Cl.
CPC ...... *A61M 39/287* (2013.01); *A61M 5/16804* (2013.01); *A61M 5/16813* (2013.01); *A61M 5/16877* (2013.01); *A61M 39/28* (2013.01); *A61M 2205/3334* (2013.01)

(58) Field of Classification Search
CPC .. A61M 2205/3334; A61M 2205/3379; A61M 39/28; A61M 39/286; A61M 39/287; A61M 5/16804; A61M 5/16813; A61M 5/16877
See application file for complete search history.

(56) References Cited

U.S. PATENT DOCUMENTS

| | | | | |
|---|---|---|---|---|
| 2,889,848 A * | 6/1959 | Redmer | .............. | A61M 39/287 137/315.07 |
| 3,289,999 A | 12/1966 | Konzak | | |
| 4,776,558 A | 10/1988 | Bellini | | |
| 5,853,398 A | 12/1998 | Lal et al. | | |
| 6,364,279 B1 * | 4/2002 | Neftel | ................. | A61M 39/287 251/4 |
| 7,074,212 B1 | 7/2006 | Florea | | |
| 2021/0077806 A1 | 3/2021 | Park et al. | | |

OTHER PUBLICATIONS

International Search Report and Written Opinion for Application No. PCT/US2023/030857, dated Nov. 29, 2023, 14 pages.

* cited by examiner

*Primary Examiner* — Shefali D Patel
(74) *Attorney, Agent, or Firm* — MASCHOFF BRENNAN

(57) ABSTRACT

A stable flow regulator assembly includes a body having a tube slot adjacent a perimeter of the body and having an opening at the perimeter to slidingly receive a portion of an intravenous (IV) tube, and a spiral slide groove extending into the body from the tube slot, wherein a width of the spiral slide groove narrows as the spiral slide groove extends further into the body. A tube arm is rotatingly coupled to the body, the tube arm having a slot open to the perimeter of the body and configured to slidingly receive the IV tube when the slot is aligned with the tube slot of the body and to regulate a flow rate through the IV tube based on a compression of the IV tube due to a position of the IV tube within the spiral slide groove. Methods of operating a stable flow regulator assembly are also provided.

16 Claims, 11 Drawing Sheets

STABLE FLOW REGULATOR ASSEMBLY

TECHNICAL FIELD

The present disclosure generally relates to a gravity intravenous (IV) set or infusion pump flow control device, and in particular a stable flow regulator assembly.

BACKGROUND

Flow controllers in the form of roller clamps are used in the medical field for intravenous (IV) applications and are typically attached to an IV tube during the manufacturing or assembly process. Such typical roller clamps are then disposed of along with the IV set or the IV tube once the IV application is complete.

Typical roller clamps allow the IV tube to be incrementally occluded by pinching the tubing as the roller clamp is tightened. A typical process is to completely close the roller clamp and regulate the fluid flow rate by rolling the roller clamp upward to open the fluid flow.

Typical roller clamps maintain the roller wheel in position based on a transient fit with the roller body, engagement of tubing with the wheel and friction of the wheel with the roller body. However, over a period at high flow rate with a typical roller clamp, the wheel drifts away from its set position and causes an inaccurate rate of fluid delivery through the tube.

Thus, it is desirable to provide a flow regulator assembly that provides structural stability to control the fluid flow consistently without variation from the adjusted or set flow rate. It is also desirable to provide a flow regulator assembly that can be added to IV tubing as needed in the field, thus eliminating the need to preassemble the flow regulator assembly with a specific IV set or IV tube. In addition, it is desirable to provide a flow regulator assembly that may be reused with different IV sets or IV tubes.

SUMMARY

One or more embodiments provide a stable flow regulator assembly including a body. The body includes a tube slot disposed adjacent a perimeter of the body, the tube slot having an opening at the perimeter to slidingly receive a portion of an intravenous (IV) tube and a spiral slide groove extending into the body from the tube slot, wherein a width of the spiral slide groove narrows as the spiral slide groove extends further into the body. The stable flow regulator assembly also includes a tube arm rotatingly coupled to the body, the tube arm having a slot open to the perimeter of the body and configured to slidingly receive the IV tube when the slot is aligned with the tube slot of the body. The stable flow regulator assembly is configured to regulate a flow rate of fluid flowing through the IV tube based on an amount of compression of the IV tube due to a position of the IV tube within the spiral slide groove.

One or more embodiments provide a stable flow regulator assembly including a body comprising a spiral slide groove extending into the body and enclosed within a perimeter of the body, wherein a width of the spiral slide groove narrows as the spiral slide groove extends further into the body. The stable flow regulator assembly also includes a plurality of teeth disposed on the perimeter of the body and a tube arm rotatingly coupled to the body, the tube arm having a slot open to the spiral slide groove and configured to slidingly receive an intravenous (IV) tube when the slot is aligned with a portion of the spiral slide groove having a width equal to or wider than a diameter of the IV tube. The stable flow regulator assembly is configured to regulate a flow rate of fluid flowing through the IV tube based on an amount of compression of the IV tube due to a position of the IV tube within the spiral slide groove.

One or more embodiments provide a stable flow regulator assembly including a body. The body includes a tube holder disposed adjacent a perimeter of the body, the tube holder having an opening to slidingly receive a portion of an intravenous (IV) tube. The body also includes a radial tube groove extending into the body around a portion of the perimeter of the body, wherein a depth of the radial tube groove decreases from a beginning end to a closing end. The stable flow regulator assembly also includes a tube arm rotatingly coupled to the body, the tube arm having a press member opposing the perimeter of the body and configured to slidingly compress the IV tube when the tube arm is rotated when the IV tube is disposed within the radial tube groove. The stable flow regulator assembly is configured to regulate a flow rate of fluid flowing through the IV tube based on an amount of compression of the IV tube due to a position of the press member relative to the IV tube within the radial tube groove.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
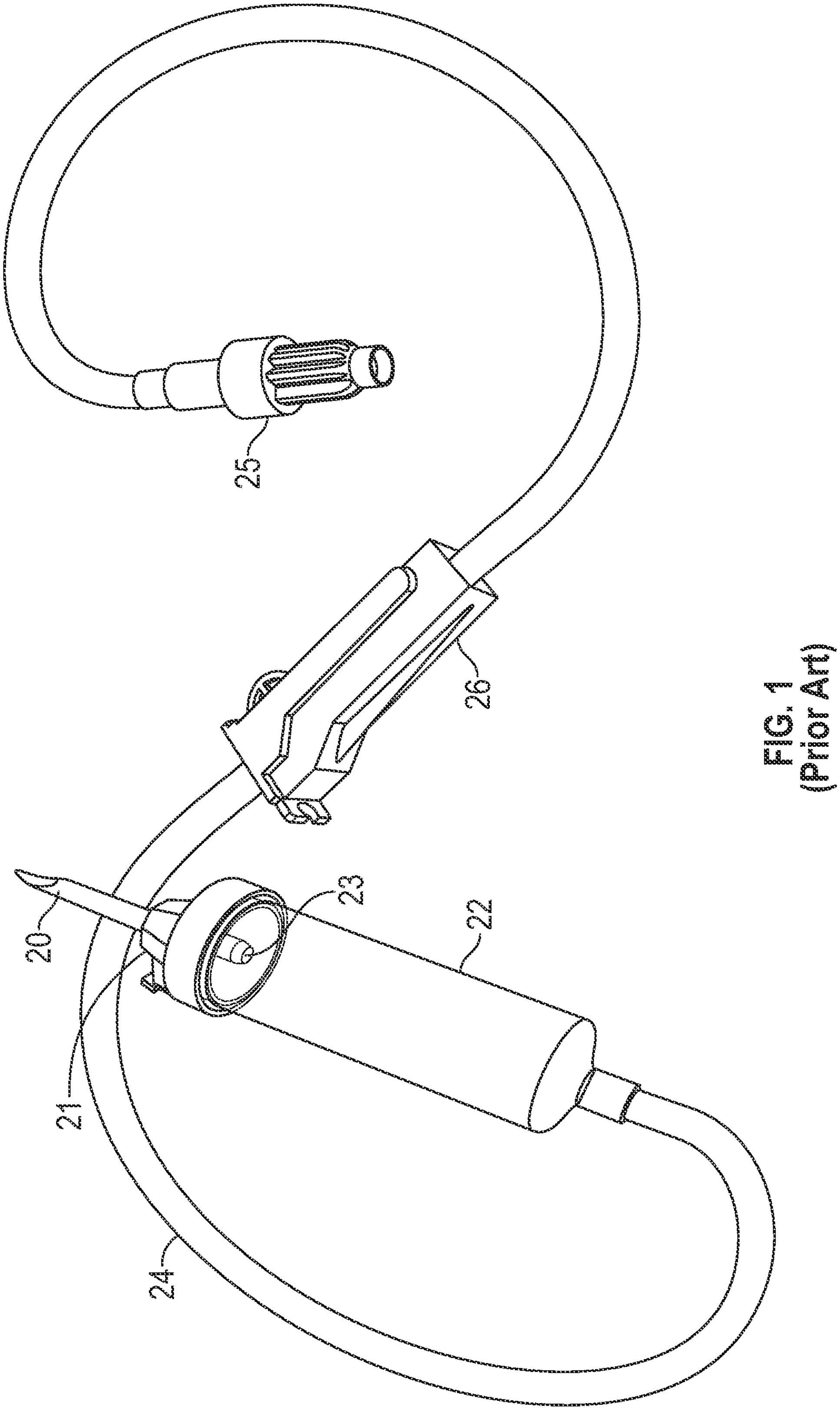
FIG. 1 (Prior Art)
FIG. 1 depicts a perspective view of an example infusion set having a typical roller clamp.

The present disclosure relates to a substitute for a roller clamp and in particular to a roller clamp for use in gravity infusion. A roller clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drop chamber 22. The vent 21 may be provided with a bacterial filter to prevent bacteria from entering the equipment.

The drop chamber 22 has a drop generator 23 at the top of the drop chamber 22 that produces drops of a certain size. Drops from the drop generator 23 fall into the drop chamber 22 such that the drop chamber 22 is partially filled with liquid. This prevents air bubbles from entering the connector tube 24, which would be harmful to a patient. A particle filter may be provided at the lower aperture of the drop chamber 22.

The connector tube 24 connects the drop chamber 22 with the patient. The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into the circulatory system of a patient (e.g., into a vein).

Between the drop chamber 22 and the Luer fitting 25 and engaging with the connector tube 24, is a roller clamp 26. The present disclosure is concerned with an improved flow regulator assembly, but a typical roller clamp 26 as known in the art will now be described for background information.

Figure 2:
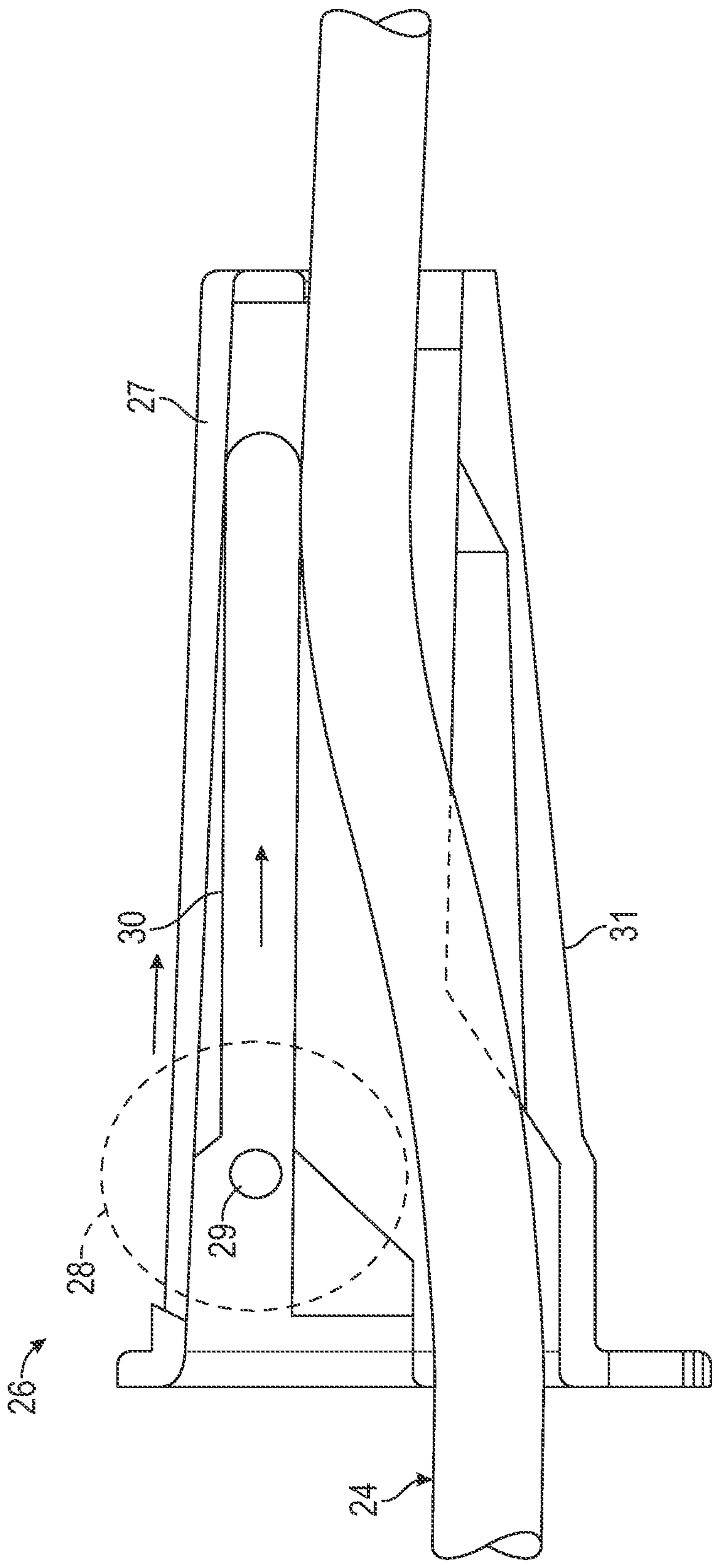
FIG. 2 (Prior Art)
FIG. 2 depicts a cross-section side view of the roller clamp of FIG. 1.

The roller clamp 26 illustrated in FIG. 2 has two opposing side walls 27 having a pair of guide grooves 30 that are aligned with each other and face each other. A flow-regulating roller 28 is provided having axially-projecting shafts 29 protruding from the centers of each side of the roller 28. The roller 28 is shown in outline for clarity. The shafts 29 of the roller 28 are captured by and seated in the guide grooves 30 so that the roller 28 can move up and down the guide grooves 30 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller 28 and a guide wall 31 that is opposed to the roller 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller 28.

Thus, rolling the roller 28 downwardly along the guide grooves 30 in the direction of the gradually closer guide wall 31 in the direction of the arrows causes the roller 28 to impinge against the connector tube 24. As the roller 28 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

Thus, the roller clamp 26 controls the flow rate through the infusion tube 24 by clamping the infusion tube 24 between the roller 28 and the guide wall 31. This provides for a course flow rate change because a small movement of the roller 28 causes a large change in the flow rate of the fluid through the tube 24. Also, the force of the fluid in the tube 24 exerts a biasing force against the roller 28, which often leads to slippage of the roller 28 (e.g., the roller 28 rolls back) from the adjusted position.

In addition, the roller clamp 26 requires preassembly with the tube 24 when the tube 24 is connected to infusion components such as the drop chamber 22 and the Luer fitting 25, for example. Thus, the roller clamp 26 cannot be added on to an IV set when the tube 24 is already connected to other components. Similarly, since the roller clamp 26 is preassembled as part of an IV set, it is typically disposed of with the IV set and not reused.

In aspects of the disclosure, stable flow regulator assemblies function as tubing clamps for IV tubing and IV sets in place of typical roller clamps. The stable flow regulator assembly provides full clamping (e.g., no flow) for a wide range of tubing sizes, provides the ability to manually and quickly release the clamping pressure with one hand to provide full open flow through the tubing, and provides the ability to gradually adjust the clamping pressure with one hand to provide for a target flow rate. The stable flow regulator assembly also provides positive locking elements for maintaining the target flow rate over time. Thus, once the stable flow regulator assembly is adjusted so that the fluid flow is set to the desired flow rate, the stable flow regulator assembly will maintain that setting for a complete fluid transfer process unless specifically adjusted to a different flow rate.

With reference to FIGS. 3-8, a stable flow regulator assembly 100 is shown. The stable flow regulator assembly 100 has a body 110 having a semi-rigid or rigid construction (e.g., hard plastic) and is dimensioned and configured to receive tubing, such as connector tube 24. The body 110 may be a circular shape as shown in the figures. The body 110 may be any desired shape (e.g., elliptical, scalloped, etc.). A tube slot 120 and a spiral slide groove 130 are disposed in the body 110. The tube slot 120 is sized to receive a desired tube size (e.g., 4 mm) such that body 110 may be slidably coupled at any location on the tube 24. For example, the tube slot 120 may be orthogonally aligned with the tube 24 and then the body 110 and the tube 24 may be slidably moved toward each other so that the tube 24 slides along the tube slot 120 and into a beginning end 132 of the spiral slide groove 130.

Here, the size of the tube slot 120 and the beginning end 132 of the spiral slide groove 130 may have a width that causes no or little compression of the tube 24, thus allowing full fluid flow through the tube 24. The spiral slide groove 130 may narrow in width as it spirals inward through the body 110 towards a closing end 134 of the spiral slide groove 130. For example, the spiral slide groove 130 may vary from a beginning width of 4 mm and narrow down to a width of 0.15 mm close to the center of the body 110. Thus, as the tube 24 is slidably moved along the spiral slide groove 130 from the beginning end 132 to the closing end 134, the tube 24 is compressed further such that the flow of fluid within the tube 24 is reduced accordingly. A friction force between the tube 24 and the sides of the spiral slide groove 130 may be sufficient to hold the tube 24 in place within the spiral slide groove 130 at any position where the tube 24 is being engaged and/or compressed by the sides of the spiral slide groove 130.

At some point of the spiral slide groove 130, the compression of the tube 24 is such that the tube 24 may be completely occluded (e.g., little or no fluid flow). The varying width of the spiral slide groove 130 provides for the ability to work with a variety of tube 24 sizes (e.g., 1 mm to 4 mm). Thus, the stable flow regulator assembly 100 may be used with a variety of different IV tubes 24 and/or IV sets. Accordingly, a single sized stable flow regulator assembly 100 may be manufactured, distributed and stored for use in any number of tubing situations, thus providing a lower cost for the flow control component of an IV set.

One or more flaps 122 may be coupled to the body 110 within the tube slot 120 or extend from the body 110 within the tube slot 120. The flaps 122 may flex inward or flex to towards the sides of the tube slot 120 as the tube 24 is slidable moved into the tube slot 120. The flaps 122 may be prevented from flexing outward from the body 110 and/or the flaps 122 may maintain an inward angular facing orientation after the tube 24 has passed the flaps 122, thus preventing the tube 24 from passing back out of body 110 through the tube slot 120.

Figure 3:
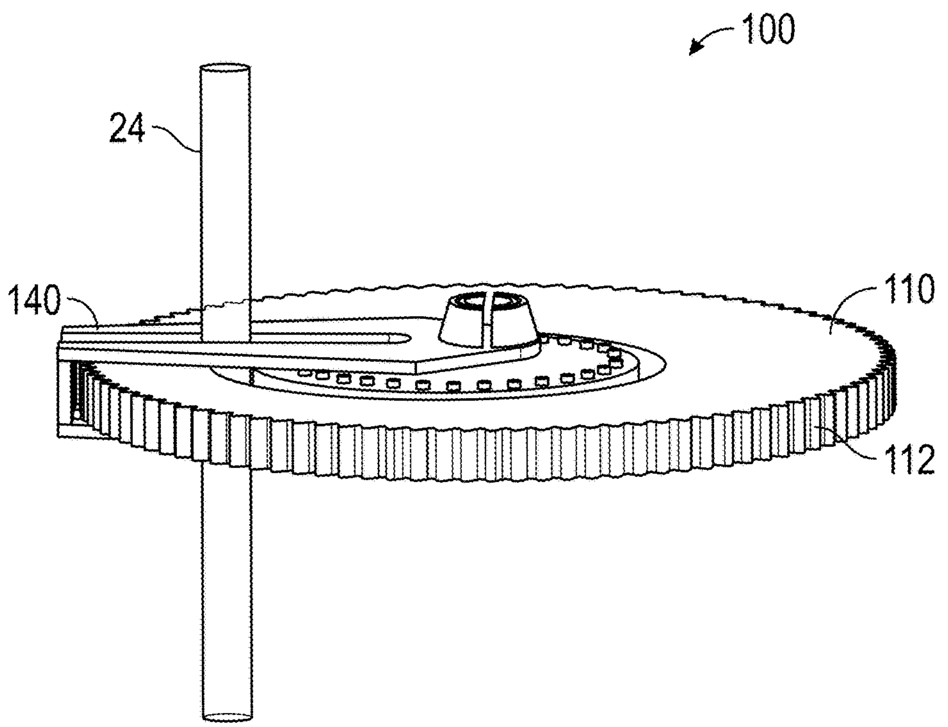
FIG. 3 depicts a perspective view of a stable flow regulator assembly coupled to an IV tube, according to aspects of the disclosure.
Figure 4:
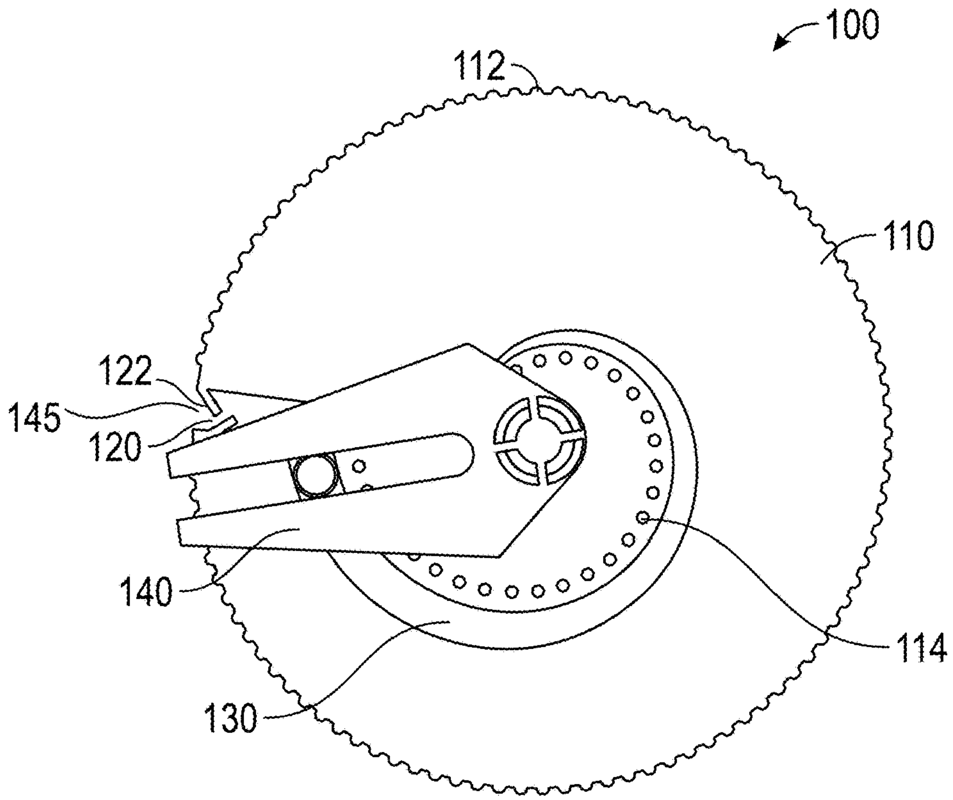
FIG. 4 depicts a top view of the stable flow regulator assembly of FIG. 3, according to aspects of the disclosure.

A grip 112 may be disposed on a perimeter of the body 110. For example, as shown in FIG. 3, the grip 112 may be multiple projections that protrude outward from the body 110 to provide a textured surface that it can be easily located, gripped and turned by hand (e.g., thumb, finger). The grip 112 may be any suitable surface (e.g., toothed, rubber, tacky material) to enhance gripping and/or turning the body 110 of the stable flow regulator assembly 100.

Holding members 114 may be disposed on one or both sides of the body 110. For example, holding members 114 may be a series of bumps or protrusions disposed along the interior side of the spiral slide groove 130. The holding members 114 may be arranged in any suitable pattern (e.g., along the exterior side of the spiral side groove 130, along the grip 112 on the perimeter of the body 110).

Figure 8:
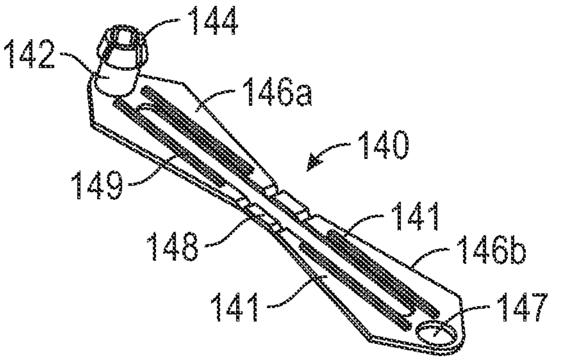
FIG. 8 depicts a perspective view of a rotation arm of the stable flow regulator assembly of FIG. 3, according to aspects of the disclosure.

A tube arm 140 is coupled to the body 110. For example, a shaft 142 of the tube arm 140 may be rotatingly coupled through a shaft hole 116 of the body 110. The shaft 142 may have a snap member 144 (e.g., canted side walls) that may flex inward as the shaft 142 passes through the shaft hole 116 and flex outward on the other side of the shaft hole 116 to secure the tube arm 140 to the body 110. As shown in FIG. 8, the tube arm 140 may have opposing arm segments **146*a*, 146*b* coupled together by hinge members 148 (e.g., living hinges). Thus, the tube arm 140 may be coupled to the body 110 by insertion of the shaft 142 on arm segment 146*a* through the shaft hole 116, folding the opposing arm segment 146*b* around the perimeter of the body 110 via the hinge members 148 and inserting the snap member 144 through a receiving hole 147 on the opposing arm segment 146*b* so that the snap member 144 secures the opposing arm segments 146*a*, 146*b* together, providing a secure rotating coupling between the tube arm 140 and the body 110**.

Arm holding members 149 (e.g., ridges, protrusions) may be disposed on the arm segments **146*a*, 146*b* in order to interact with the holding members 114 on the body 110. For example, the arm holding members 149 may be configured to ride up and over an engaged holding member 114 based on a turning force exerted by rotating the tube arm 140 in relation to the body 110. Thus, arm holding member 149 may be maintained between two holding members 114 until a sufficient force is exerted on the tube arm 140 to move the arm holding member 149 past one of the two holding members 114. In this way, the interaction between the arm holding members 149 and the holding members 114 provide an additional securing element over and above the friction force between the tube 24 and the sides of the spiral slide groove 130**.

The tube arm 140 also includes a slot 145 configured to receive the tube 24. The slot 145 of the tube arm 140 may be the same size (e.g., width) as the tube slot 120 in the body 110. Thus, when the tube 24 is disposed within the slot 145, the tube 24 is compressed not at all or very little by the tube arm 140, which provides for most or all of the compression of the tube 24 to be based on the spiral slide groove 130. The arm segments 146*a*, 146*b* and the hinge members 148 may collectively include side portions 141 that define the slot 145. For example, when the tube arm 140 is in an expanded position (e.g., not coupled to the body 110), the arm segments 146*a*, 146*b* and the hinge members 148 may be linearly aligned and defined the slot 145 as an enclosed channel. When the tube arm 140 is fully coupled to the body 110 (e.g., folded over the perimeter of the body 110 and snapped together), the slot 145 is then open to the perimeter of the body 110, thus providing a path for the tube 24 to slide into the body 110 when the slot 145 is aligned with the tube slot 120.

In aspects of the disclosure, indicator markings 118 may be disposed on the body 110 (see FIG. 7) to provide visual indications of the expected fluid flow rates at various positions of the tube 24 in the spiral slide groove 130. The indicator markings 118 may be any suitable markings (e.g., text, graphics, shapes, colors) that quickly and easily convey the fluid flow rate of the tube 24 at that position in the spiral slide groove 130.

Figure 5:
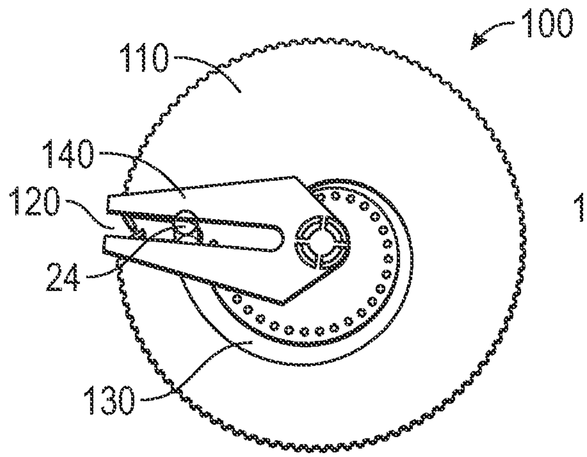
FIG. 5 depicts a top perspective view of the stable flow regulator assembly of FIG. 3 in an open flow rate position, according to aspects of the disclosure.
Figure 6:
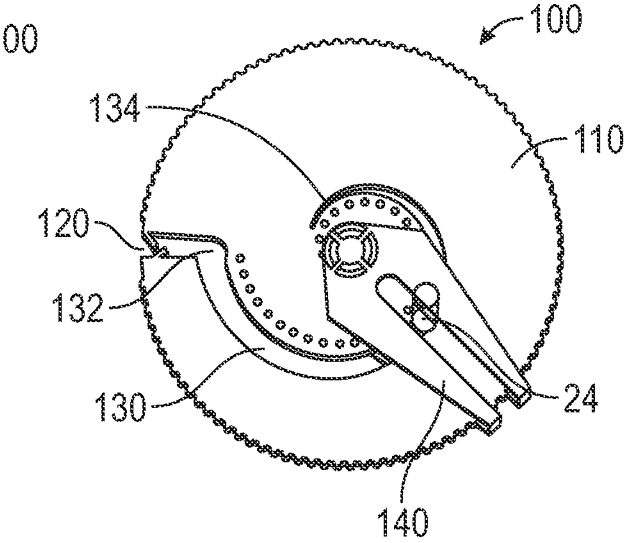
FIG. 6 depicts a top perspective view of the stable flow regulator assembly of FIG. 3 in an adjusted flow rate position, according to aspects of the disclosure.
Figure 7:
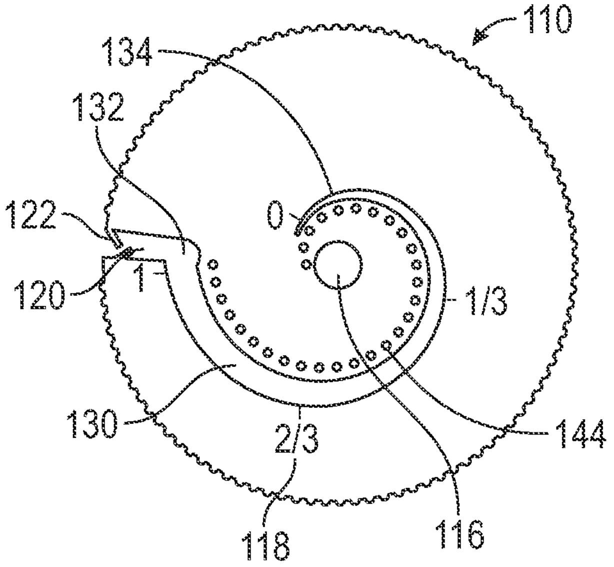
FIG. 7 depicts a top view of a body of the stable flow regulator assembly of FIG. 3, according to aspects of the disclosure.
Figure 15:
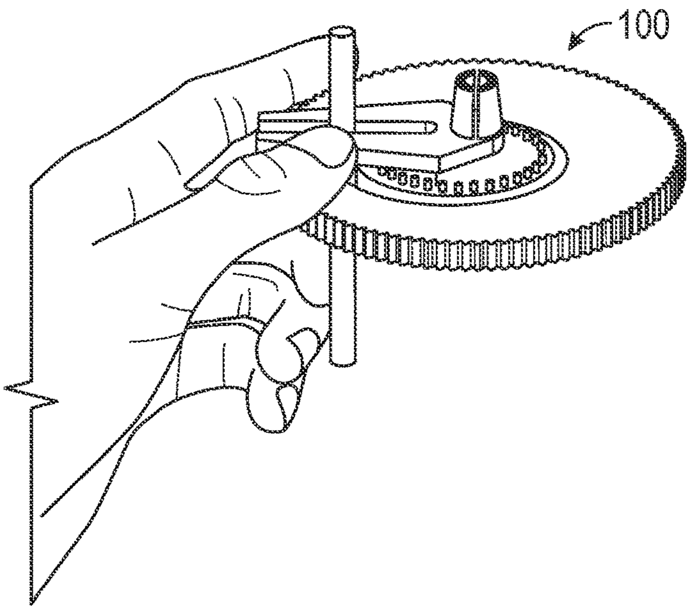
FIG. 15 illustrates a one handed grip and operation of a stable flow regulator assembly, according to aspects of the disclosure.
Figure 16:
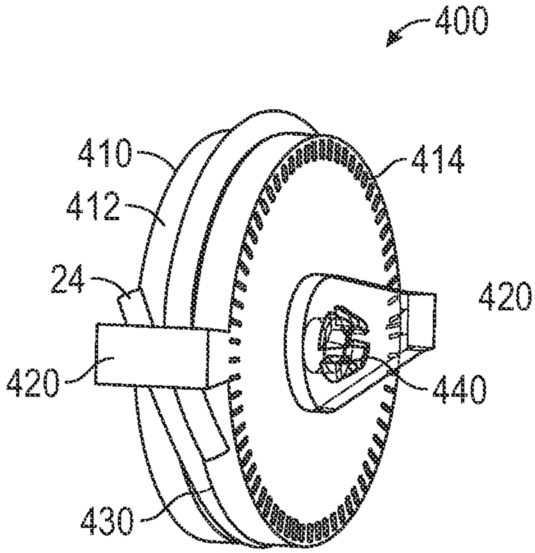
FIG. 16 depicts a perspective view of a stable flow regulator assembly coupled to an IV tube, according to aspects of the disclosure.
Figure 17:
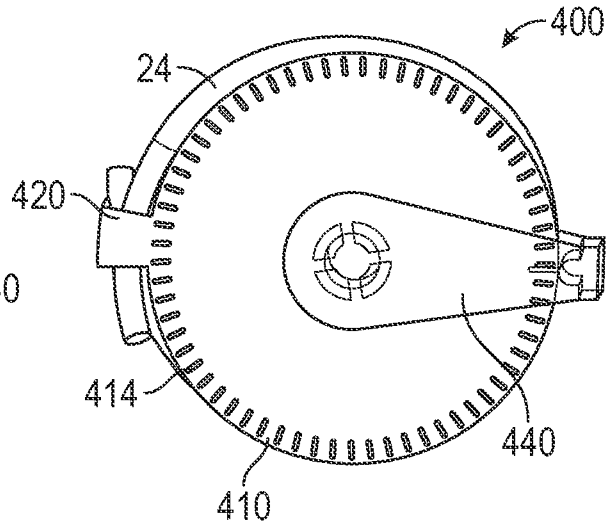
FIG. 17 depicts a top view of the stable flow regulator assembly of FIG. 16, according to aspects of the disclosure.

In use, a combined or assembled body (e.g., body 110) and tube arm (e.g., tube arm 140) of a stable flow regulator assembly (e.g., stable flow regulator assembly 100) is slid onto a tube (e.g., tube 24). Here, the tube is slid through an opening of the body (e.g., tube slot 120) and an opening of the tube arm (e.g., slot 145), and then into a groove (e.g., spiral slide groove 130), where the tube is in an open flow/uncompressed state (see. FIG. 5). The tube is then slid along the groove until the tube is squeezed (e.g., occluded, compressed) an amount that causes a desired fluid flow rate through the tube (see FIG. 6). For example, the tube arm may be gripped on both sides of the body by a single hand (e.g., between a thumb and index finger) and the body rotated in relation to the tube arm by another finger of the same hand (e.g., the forefinger) as shown in FIG. 15. Thus, the stable flow regulator assembly may be quickly and easily operated with one hand, leaving the other hand of a user available to handle other tasks.

As the body is turned (e.g., body 110 rotated in relation to the tube arm 140), the tube slides along the groove and is either compressed further (e.g., compressed between narrowing sides of spiral slide groove 130) or expands (e.g., expands out due to widening sides of spiral slide groove 130). Thus, the compression pressure on the tube is either increased or reduced based on the direction the tube is moved in the groove, and either decreased or increased fluid flow may pass through the tube, respectively. The flow rate may be adjusted to different flow rates by turning the body in relation to the tube arm, thus changing the amount of compression of the tube by the sides of the groove. In other words, the amount of tube compression is dependent upon the position of the tube in the groove, which provides for different flow rates to be selected.

In aspects of the disclosure, stable flow regulator assembly 100 may provide a variety of benefits in comparison to typical roller clamps. For example, stable flow regulator assembly 100 provides full clamping for a wide range of tubing sizes by having a consistently narrowing groove to provide for target percentage compression ranges across a variety of tube thicknesses or widths. In aspects of the disclosure, the stable flow regulator assembly 100 prevents or minimizes fluid flow rate drift once the tube is set in a position within the body 110. Also, stable flow regulator assembly 100 provides a way to manually and quickly release all of the compression pressure to allow full open flow through the tube (e.g., tube 24 moved to the beginning end 132 of the spiral slide groove 130).

In addition, stable flow regulator assembly 100 provides a way to gradually release the compression pressure to allow a target flow rate to be achieved (e.g., tube 24 moved along the spiral slide groove 130 toward the beginning end 132). Further, stable flow regulator assembly 100 provides an ergonomic human interface (e.g., body 110 and tube arm 140) that provides for efficient and simple operation with a single hand.

Figure 9:
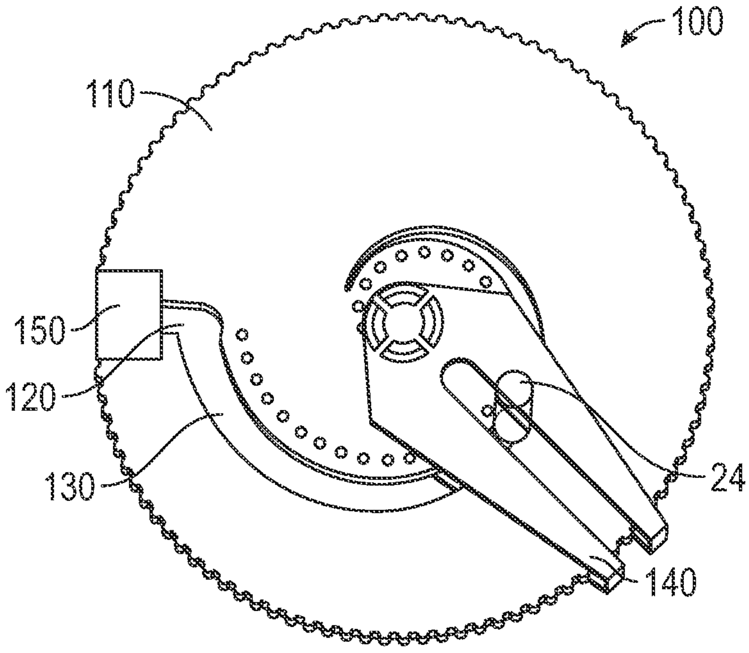
FIG. 9 depicts a perspective view of a stable flow regulator assembly coupled to an IV tube, according to aspects of the disclosure.

In aspects of the disclosure, as shown in FIG. 9, the stable flow regulator assembly 100 may include a locking member 150 that may be coupled to the body 110 in place of or in addition to the flaps 122. For example, the locking member 150 may be a removable clip that is snapped into place over the tube slot 120 once the tube 24 is far enough within the tube slot 120 or is within the spiral slide groove 130, thus preventing removal of the tube 24 from the body 110. When use of the tube 24 or the IV set the tube 24 is part of is finished, the locking member 150 may be opened (e.g., unclipped) so that the stable flow regulator assembly 100 may be removed from the tube 24 and reused with another tube or IV set. The locking member 150 may be any suitable structure (e.g., rotating arm, rotating clip, removable clip, adhesive tape).

Figure 10:
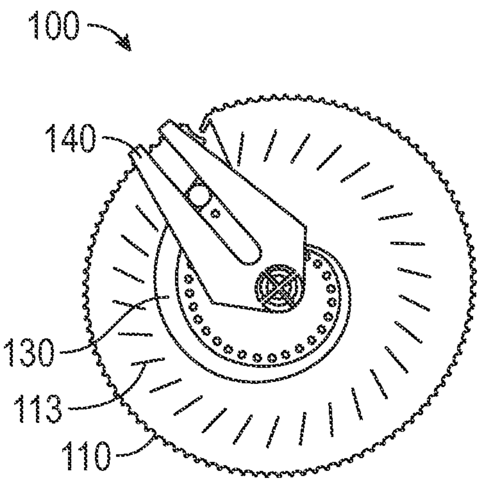
FIG. 10 depicts a perspective view of a stable flow regulator assembly, according to aspects of the disclosure.

In aspects of the disclosure, as shown in FIG. 10, the stable flow regulator assembly 100 may include ratchet teeth 113 disposed on one or both sides of the body 110. The ratchet teeth 113 may be configured to interact with the tube arm 140. For example, the arm holding members 149 may be sized and shaped (e.g., cantilevered, angled) to provide less resistance in one rotation direction of the tube arm 140 than in the opposite rotation direction of the tube arm 140, based on the engagement of the arm holding members 149 with the ratchet teeth 113. Here, the higher resistance rotational direction may be configured to prevent or minimize rotational drift of the tube arm 140 due to fluid flow pressure in the tube 24. Thus, the ratchet teeth 113 may be used in addition to the holding members 114, or in place of the holding members 114 to keep the tube arm 140 at the desired position, thus keeping the compression on the tube 24 and the resulting fluid flow rate at the set level. In aspects of the disclosure, the resistance from the ratchet teeth 113 and/or the holding members 114 on the tube arm 140 may be overcome by applying enough force on the tube arm 140 or the body 110 (e.g., rotating the body 110 with respect to the tube arm 140 by hand). Thus, the position of the tube arm 140 may be adjusted to any suitable position within the spiral slide groove 130 in order to obtain a desired fluid flow rate in the tube 24.

Figure 11:
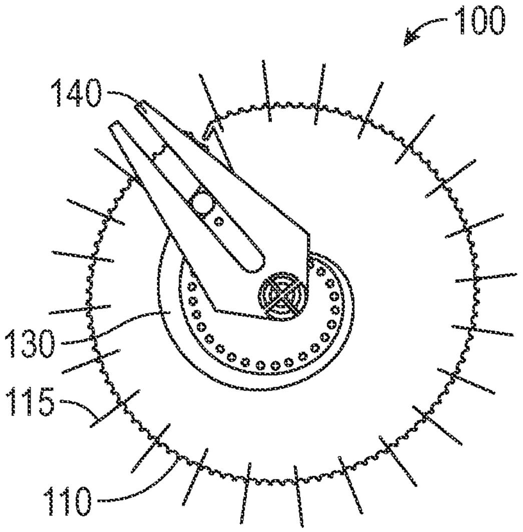
FIG. 11 depicts a top view of a stable flow regulator assembly coupled to an IV tube, according to aspects of the disclosure.

In aspects of the disclosure, as shown in FIG. 11, the stable flow regulator assembly 100 may include flaps 115 disposed on one or both sides of the body 110 near the perimeter of the body 110. The flaps 115 may be configured to interact with the tube arm 140. For example, the opposing arm segments 146*a*, 146*b* may extend out past the perimeter of the body 110 and the arm holding members 149 may be sized and shaped (e.g., cantilevered, angled) to provide less resistance in one rotation direction of the tube arm 140 than in the opposite rotation direction of the tube arm 140, based on the engagement of the arm holding members 149 with the flaps 115. Here, the higher resistance rotational direction may be configured to prevent or minimize rotational drift of the tube arm 140 due to fluid flow pressure in the tube 24. Thus, the flaps 115 may be used in addition to the holding members 114, or in place of the holding members 114 to keep the tube arm 140 at the desired position, thus keeping the compression on the tube 24 and the resulting fluid flow rate at the set level. In aspects of the disclosure, the resistance from the flaps 115 and/or the holding members 114 on the tube arm 140 may be overcome by applying enough force on the tube arm 140 or the body 110 (e.g., rotating the body 110 with respect to the tube arm 140 by hand). In aspects of the disclosure, the flaps 115 may be rigid, semi-rigid or flexible and may be configured to provide better rotation of the body 110 relative to the tube arm 140. Thus, the position of the tube arm 140 may be adjusted to any suitable position within the spiral slide groove 130 utilizing the flaps 115 in order to obtain a desired fluid flow rate in the tube 24.

Figure 12:
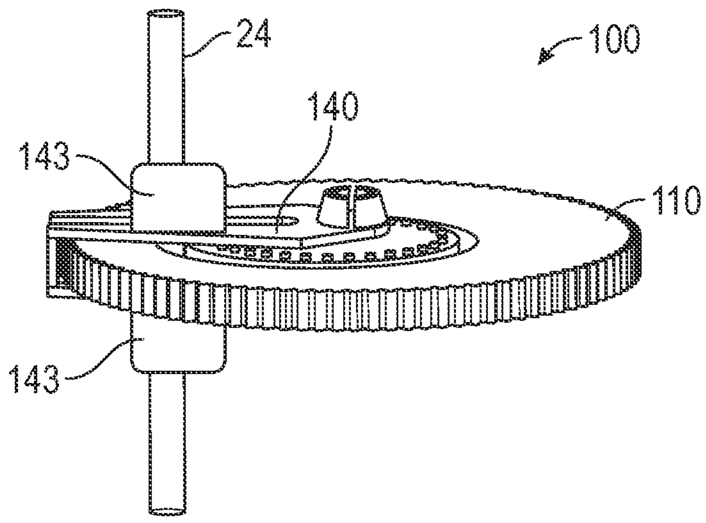
FIG. 12 depicts a top view of a stable flow regulator assembly coupled to an IV tube, according to aspects of the disclosure.

In aspects of the disclosure, as shown in FIG. 12, the stable flow regulator assembly 100 may include flaps 143 disposed on one or both sides of the tube arm 140. The flaps 143 may be rigid or semi-rigid to provide better rotation of the body 110 relative to the tube arm 140. For example, the flaps 143 may provide more surface area of the tube arm 140 to provide extra support for gripping of the stable flow regulator assembly 100 to allow the body 110 to be rotated more easily.

Figure 13:
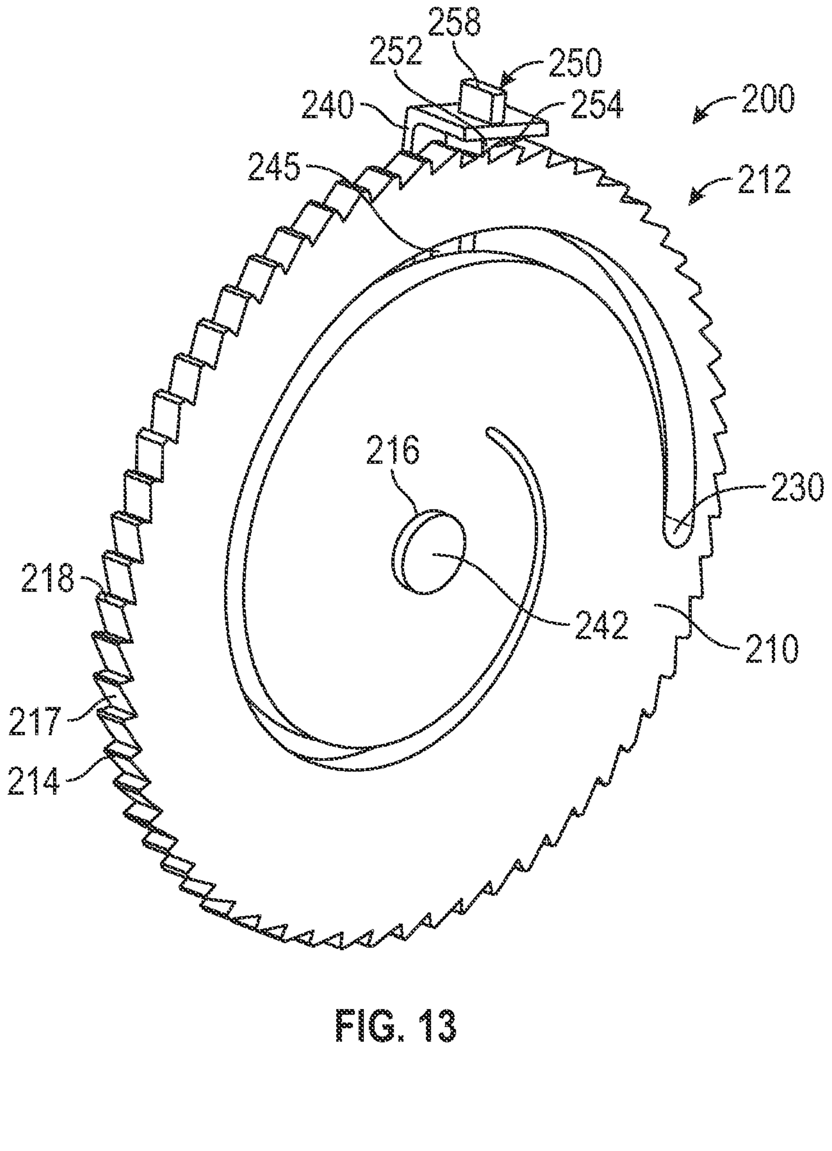
FIG. 13 depicts a perspective view of a stable flow regulator assembly coupled to an IV tube, according to aspects of the disclosure.

In aspects of the disclosure, as shown in FIG. 13, a stable flow regulator assembly 200 may include a body 210, an enclosed spiral slide groove 230 and a tube arm 240 rotatingly coupled to the body 210 via a shaft 242 disposed through a shaft hole 216. A grip 212 on the perimeter of the body 210 may be in the form of teeth 214 having sloped or cantilevered portions 217 and vertical (e.g., orthogonal) portions 218. An outer end of the tube arm 240 may include an arm holding member 250 that includes a stop member 252 extending inward and configured to engage the grip 212. For example, the stop member 252 may have a sloped or cantilevered protrusion 254 that may ride along the sloped or cantilevered portions 217 of the teeth 214 in one rotational direction and a vertical stop portion 256 that may butt up against the vertical portions 218 of the teeth 214 in the opposing rotational direction. A grip member 258 of the stop member 252 may extend outward to provide an ergonomic gripping surface for moving the tube arm 240. The tube arm 240 also includes a slot 245 configured to receive the tube 24.

In use the tube 24 may be inserted into the spiral slide groove 230 through the slot 245 (e.g., like threading a needle) and the tube arm 240 may be rotated by pushing on the grip member 258 in the desired direction to rotate the tube arm 240 and thereby slide the tube 24 along in the spiral slide groove 230. The stop member 252 may move along the teeth 214 in a ratchet manner. Once the tube 24 is in the desired position in the spiral slide groove 230, expansion forces from fluid flow in the tube 24 may tend to try to force the tube arm 240 towards the wider end of the spiral slide groove 230, but the vertical stop portion 256 butting up against the vertical portion 218 of the adjacent tooth 214 prevents movement of the tube arm 240 and the tube 24 in that direction. Similarly, the further compressive force of moving the tube 24 in the narrowing direction of the spiral slide groove 230 will also prevent the tube arm 240 and the tube 24 from moving in that direction. Thus, drift of the tube 24 from the set position in the spiral slide groove 230 is prevented or minimized.

Figure 14:
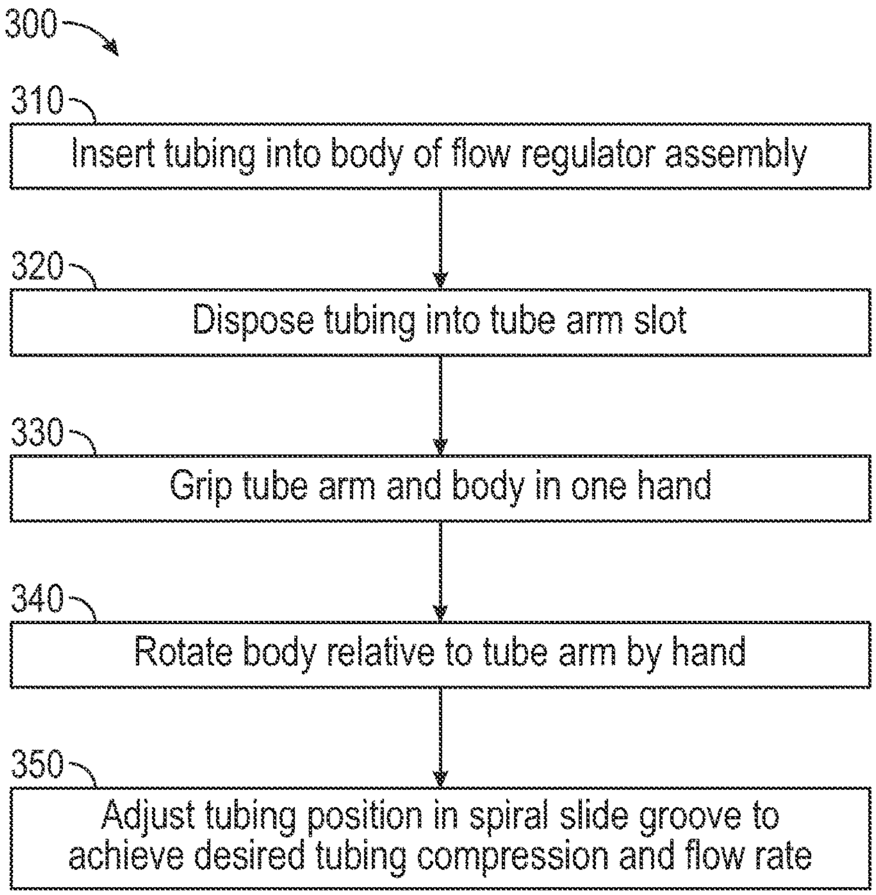
FIG. 14 illustrates a method of operating a stable flow regulator assembly, according to aspects of the disclosure.

With reference to FIG. 14, a method 300 of operating a stable flow regulator assembly (e.g., stable flow regulator assembly 100, 200) is provided. In step 310, tubing (e.g., IV tube 24) is placed or inserted into a body (e.g., body 110, 210) such that the tubing is disposed within a spiral slide groove (e.g., groove 130, 230). The tubing is further disposed in a slot (e.g., tube arm slot 145, 245) in a tube arm (e.g., tube arm 140, 240) that is rotationally coupled to the body, in step 320.

In step 330, as shown in FIG. 15, the stable flow regulator assembly is gripped by hand such that the tube arms are gripped on both sides of the body (e.g., by a thumb and a middle finger of one hand) and the body is engaged by another finger (e.g., index finger of the same hand). The body is rotated by hand (e.g., by turning the body relative to the tube arm), in step 340.

In step 350, the tubing position in the spiral slide groove is adjusted to cause the desired flow rate by rotating the body relative to the tube arm until the slot width of the spiral slide groove compresses the tubing a suitable amount to achieve the desired flow rate. For example, regarding stable flow regulator assembly 100, 200, as the body 110, 210 is turned relative to the tube arm 140, 240, the width of the spiral slide groove 130, 230 narrows or widens, depending upon which way the body 110 is turned, causing the tube 24 within the spiral slide groove 130, 230 to be compressed more or less, respectively.

Non-pressure rated tubing typically is made from similar wall thicknesses. In aspects of the disclosure, a stable flow regulator assembly 100, 200 may include varying amounts of compression (e.g., varying gap size of the spiral slide groove 130, 230). Thus, the stable flow regulator assembly 100, 200 may work with small, medium and large tubing 24 diameters or thicknesses. For example, a gap sizing variation may include small, medium and large gap widths of 0.027 mm, 0.036 mm and 0.050 mm, respectively. As another example, a gap sizing variation may include small, medium and large gap widths of 0.015 mm, 0.020 mm and 0.030 mm, respectively. Thus, the gap sizing may be designed depending upon the desired sizes of tubing 24 that are anticipated and/or needed. Accordingly, tubing with the largest desired width may be uncompressed at the widest end of the spiral slide groove 130, 230 and fully compressed halfway along the spiral slide groove 130, 230, while tubing with a smaller width may be uncompressed one third along the spiral slide groove 130, 230 and fully compressed two thirds along the spiral slide groove 130, 230, for example.

In aspects of the disclosure, the outward or expansive force from the fluid flow and/or the expansive nature of the tube material is radially outward. Thus, no reaction force from the compressed tube acts on the tube arm along the path of the spiral slide groove, and in order to rotate the tube arm relative to the body a tangential force needs to be applied by a user. In aspects of the disclosure, the stable flow regulator assembly may be configured to work with and/or be engaged by an automated device. For example, the tube arm segments on both side of the body may be gripped or clamped by a motorized device and a pushing member may be engaged with the body such that turning the motor causes the pushing member to correspondingly turn the body relative to the tube arm.

In aspects of the disclosure, a positive locking element (e.g., holding members 114 and arm holding members 149) may be provided to prevent or minimize accidental movement of the body relative to the tube arm. In aspects of the disclosure, the positive locking element may provide audible feedback when the body is rotated relative to the tube arm. For example, the movement of the arm holding members 149 against the holding members 114 may provide a ticking sound (e.g., like rotation of a padlock).

With reference to FIGS. 16-23, a stable flow regulator assembly 400 is shown. The stable flow regulator assembly 400 has a body 410 having a semi-rigid or rigid construction (e.g., hard plastic) and is dimensioned and configured to receive tubing, such as connector tube 24. The body 410 may be a circular shape as shown in the figures. The body 410 may be any desired shape (e.g., elliptical, scalloped, etc.). A tube holder 420 may extend out from a perimeter 412 of the body, the tube holder 420 having an opening configured to receive the tube 24. A radial tube groove 430 is disposed in the body 410, such as around a portion of the perimeter 412 of the body 410. The radial tube groove 430 is sized to receive a desired tube size (e.g., 4 mm) such that body 410 may be coupled at any location on the tube 24. For example, the radial tube groove 430 may be axially aligned with the tube 24 and then the tube 24 may be wound around the body 410 so that the tube 24 slides into the radial tube groove 430 around the perimeter 412.

Here, the size of the radial tube groove 430 at a beginning end 432 may have a depth that fully receives the tube 24 and thus causes no or little compression of the tube 24 and allows full fluid flow through the tube 24. The radial tube groove 430 may decrease in depth as it winds around the perimeter 412 of the body 410 towards a closing end 434 of the radial tube groove 430. For example, the radial tube groove 430 may vary from a beginning depth of 4 mm and decrease down to a depth of 0.15 mm at closing end 434. Thus, when the tube 24 is disposed in the radial tube groove 430 from the beginning end 432 to the closing end 434, the tube 24 may be compressed further such that the flow of fluid within the tube 24 is reduced accordingly. A tension force on the tube 24 disposed in the radial tube groove 430 and/or a friction force from the tube holder 420 on the tube 24 may be sufficient to hold the tube 24 in place within the radial tube groove 430 around the perimeter 412 of the body 410.

At some point of the radial tube groove 430, the compression of the tube 24 is such that the tube 24 may be completely occluded (e.g., little or no fluid flow). The varying depth of the radial tube groove 430 provides for the ability to work with a variety of tube 24 sizes (e.g., 1 mm to 4 mm). Thus, the stable flow regulator assembly 400 may be used with a variety of different IV tubes 24 and/or IV sets. Accordingly, a single sized stable flow regulator assembly 400 may be manufactured, distributed and stored for use in any number of tubing situations, thus providing a lower cost for the flow control component of an IV set.

Figure 21:
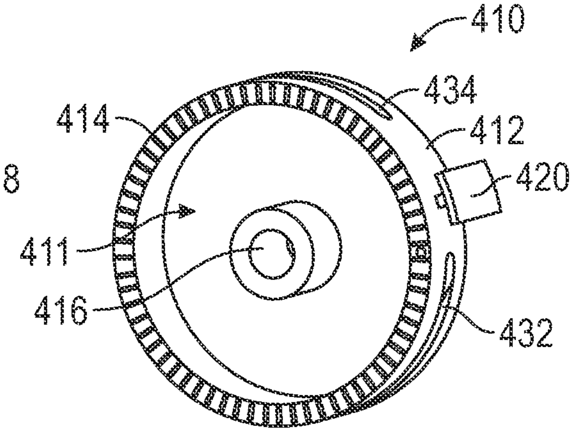
FIG. 21 depicts another perspective view of the body of FIG. 20, according to aspects of the disclosure.

Holding members 414 may be disposed on one or both sides of the body 410. For example, holding members 414 may be a series of bumps or protrusions disposed along the perimeter 412 of the body 410. The holding members 414 may be arranged in any suitable pattern (e.g., evenly spaced along the perimeter 412). The body 410 may have an open cavity 411 as shown in FIG. 21. The body 410 may be solid or any other suitable construction, for example.

Figure 22:
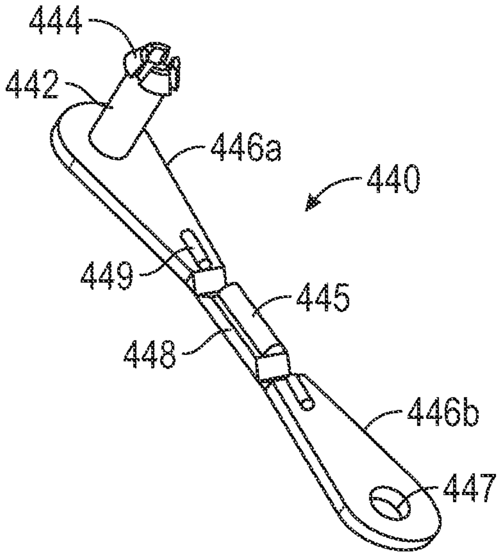
FIG. 22 depicts a perspective view of a rotation arm of the stable flow regulator assembly of FIG. 16, according to aspects of the disclosure.
Figure 23:
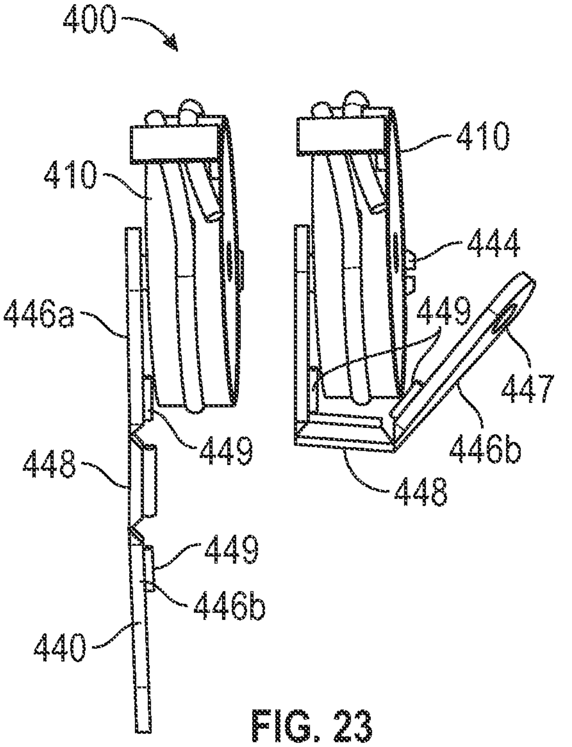
FIG. 23 depicts side views of assembly of the rotation arm of FIG. 22 to the body of FIG. 20, according to aspects of the disclosure.

A tube arm 440 is coupled to the body 410. For example, a shaft 442 of the tube arm 440 may be rotatingly coupled through a shaft hole 416 of the body 410. The shaft 442 may have a snap member 444 (e.g., canted side walls) that may flex inward as the shaft 442 passes through the shaft hole 46 and flex outward on the other side of the shaft hole 416 to secure the tube arm 440 to the body 410. As shown in FIG. 22, the tube arm 440 may have opposing arm segments 446*a*, 446*b* coupled together by a hinge member 448 (e.g., living hinge). Thus, the tube arm 440 may be coupled to the body 410 by insertion of the shaft 442 on arm segment 446*a* through the shaft hole 416, folding the opposing arm segment 446*b* around the perimeter of the body 410 via the hinge member 448 (see FIG. 23) and inserting the snap member 444 through a receiving hole 447 on the opposing arm segment 446*b* so that the snap member 444 secures the opposing arm segments 446*a*, 446*b* together, providing a secure rotating coupling between the tube arm 440 and the body 410.

Arm holding members 449 (e.g., ridges, protrusions) may be disposed on the arm segments 446*a*, 446*b* in order to interact with the holding members 414 on the body 410. For example, the arm holding members 449 may be configured to ride up and over an engaged holding member 414 based on a turning force exerted by rotating the tube arm 440 in relation to the body 410. Thus, arm holding member 449 may be maintained between two holding members 414 until a sufficient force is exerted on the tube arm 440 to move the arm holding member 449 past one of the two holding members 414. In this way, the interaction between the arm holding members 449 and the holding members 414 provide an additional securing element over and above the tension and friction force exerted on the tube 24 in the radial tube groove 430.

The tube arm 440 may also include a press member 445 configured to press the tube 24. The press member 445 of the tube arm 440 may be the same size (e.g., length) as the thickness of the body 110, the width of the hinge member 448 or any other suitable length. The press member 445 may be semi-cylindrical in shape as shown in FIG. 22, or any other suitable shape for pressing in on the tube 24. Thus, when the tube 24 is disposed within the radial tube groove 430, the tube 24 is compressed not at all or very little by the press member 445 of the tube arm 440 when the press member 445 is positioned over the beginning end 432, whereas the tube 24 is compressed completely or very greatly by the press member 445 when the press member 445 is positioned over the closing end 434. Here, the rounded surface of the press member 445 may provide for the press member 445 to slidably move along the tube 24 as the tube arm 440 is rotated in relation to the body 410, or the body 410 is rotated in relation to the tube arm 440, or both.

In aspects of the disclosure, indicator markings 418 may be disposed on the body 410 (see FIG. 20) to provide visual indications of the expected fluid flow rates at various positions of press member 445 along the tube 24 in the radial tube groove 430. The indicator markings 418 may be any suitable markings (e.g., text, graphics, shapes, colors) that quickly and easily convey the fluid flow rate of the tube 24 at that position of the tube arm 440 along the radial tube groove 430.

Figure 18:
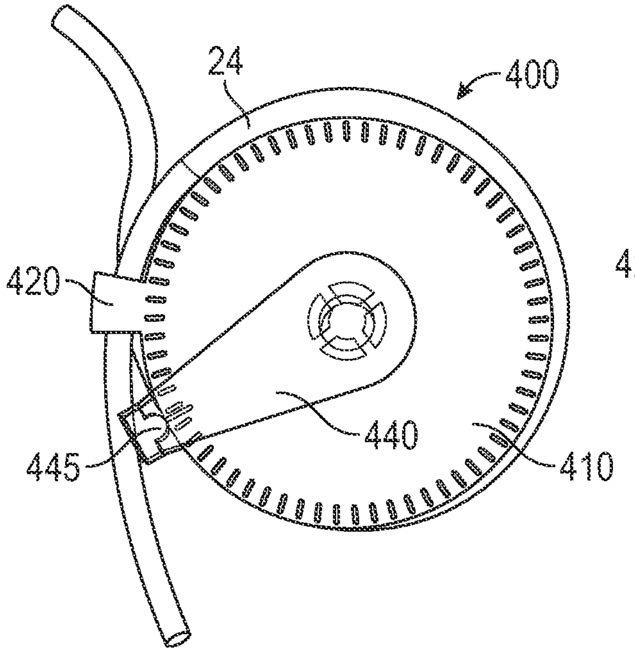
FIG. 18 depicts a top perspective view of the stable flow regulator assembly of FIG. 16 in an open flow rate position, according to aspects of the disclosure.
Figure 19:
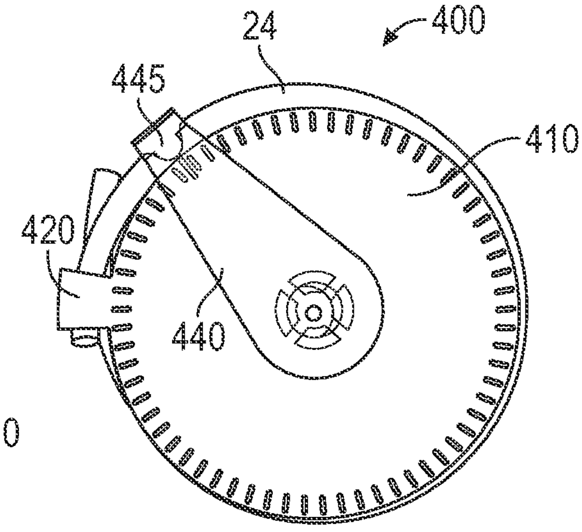
FIG. 19 depicts a top perspective view of the stable flow regulator assembly of FIG. 16 in an adjusted flow rate position, according to aspects of the disclosure.
Figure 20:
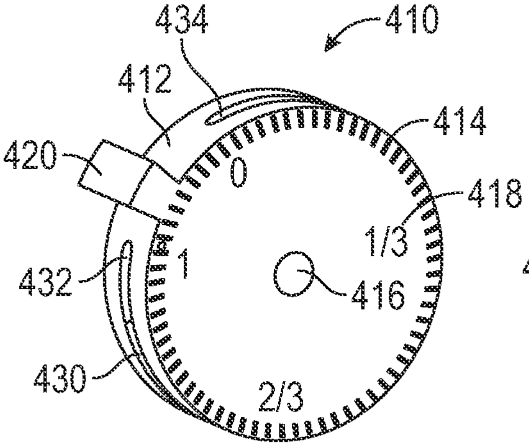
FIG. 20 depicts a perspective view of a body of the stable flow regulator assembly of FIG. 16, according to aspects of the disclosure.
Figure 27:
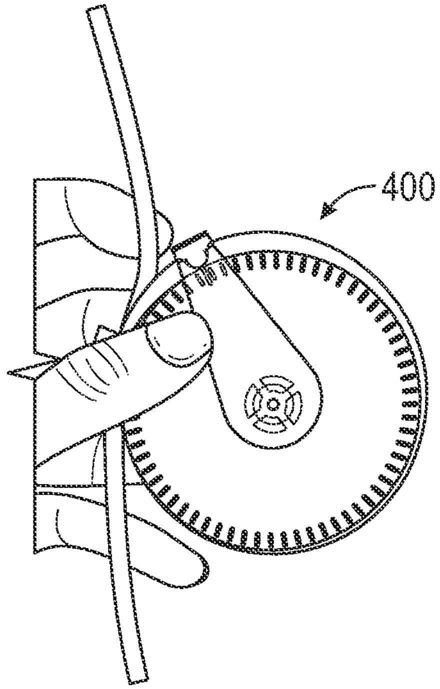
FIG. 27 illustrates a one handed grip and operation of a stable flow regulator assembly, according to aspects of the disclosure.

In use, a combined or assembled body (e.g., body 410) and tube arm (e.g., tube arm 440) of a stable flow regulator assembly (e.g., stable flow regulator assembly 400) receives a tube (e.g., tube 24). Here, the tube is slid onto and wound around a perimeter of the body (e.g., perimeter 412) and positioned into a groove (e.g., radial tube groove 430). The portions of the tube not resting in the groove are tucked under a tube holder (e.g., tube holder 420) to hold the tube in place around the perimeter of the body. Here the tube may be in an open flow/uncompressed state (see. FIG. 18) as the press member (e.g., press member 445) may have no or little contact with the tube due to the depth of the groove. The tube arm is rotated relative to the body until the tube is squeezed (e.g., occluded, compressed) by a pressing protrusion (e.g., press member 445) an amount that causes a desired fluid flow rate through the tube (see FIG. 19). For example, the tube arm may be gripped on both sides of the body by a single hand (e.g., between a thumb and index finger) and the body rotated in relation to the tube arm by another finger of the same hand (e.g., the forefinger) as shown in FIG. 27. Thus, the stable flow regulator assembly may be quickly and easily operated with one hand, leaving the other hand of a user available to handle other tasks.

As the body is turned (e.g., body 410 rotated in relation to the tube arm 440), the press member slides along the tube in the groove and the tube is either compressed further (e.g., compressed between the press member 445 and shallower depths of radial tube groove 430) or expands (e.g., expands out due to increasing depths of radial tube groove 430). Thus, the compression pressure on the tube is either increased or reduced based on the direction the tube arm is moved around the groove, and either decreased or increased fluid flow may pass through the tube, respectively. The flow rate may be adjusted to different flow rates by turning the body in relation to the tube arm, thus changing the amount of compression of the tube by the depth of the groove. In other words, the amount of tube compression is dependent upon the position of the press member against the tube in the groove, which provides for different flow rates to be selected.

In aspects of the disclosure, stable flow regulator assembly 400 may provide a variety of benefits in comparison to typical roller clamps. For example, stable flow regulator assembly 400 provides full clamping for a wide range of tubing sizes by having a consistently shallowing groove to provide for target percentage compression ranges across a variety of tube thicknesses or widths. In aspects of the disclosure, the stable flow regulator assembly 400 prevents or minimizes fluid flow rate drift once the tube arm 440 is set in a position on the body 410. Also, stable flow regulator assembly 400 provides a way to manually and quickly release all of the compression pressure to allow full open flow through the tube (e.g., tube arm 440/press member 445 moved to the beginning end 432 of the radial tube groove 430).

In addition, stable flow regulator assembly 400 provides a way to gradually release the compression pressure to allow a target flow rate to be achieved (e.g., tube arm 440 moved along the radial tube groove 430 toward the beginning end 432). Further, stable flow regulator assembly 400 provides an ergonomic human interface (e.g., body 410 and tube arm 440) that provides for efficient and simple operation with a single hand.

Figure 24:
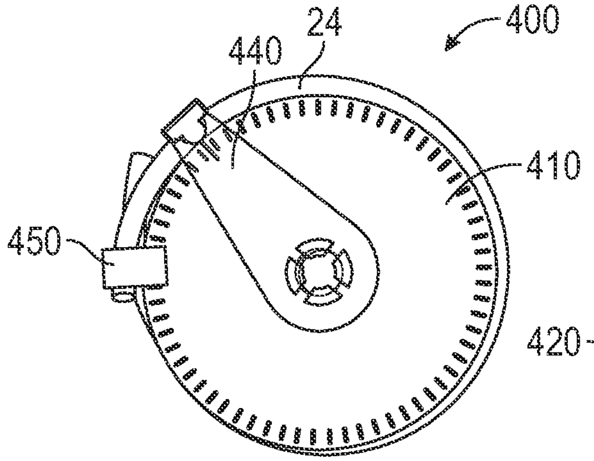
FIG. 24 depicts a perspective view of a stable flow regulator assembly coupled to an IV tube, according to aspects of the disclosure.

In aspects of the disclosure, as shown in FIG. 24, the stable flow regulator assembly 400 may include a locking member 450 that may be coupled to the body 410 in place of or in addition to the tube holder 420. For example, the locking member 450 may be a removable clip that is snapped into place over the perimeter 412 once the tube 24 is disposed within the radial tube groove 430, thus preventing removal of the tube 24 from the body 410. When use of the tube 24 or the IV set the tube 24 is part of is finished, the locking member 450 may be opened or removed (e.g., unclipped, pulled off) so that the stable flow regulator assembly 400 may be removed from the tube 24 and reused with another tube or IV set. The locking member 450 may be any suitable structure (e.g., rotating arm, rotating clip, removable clip, adhesive tape).

Figure 25:
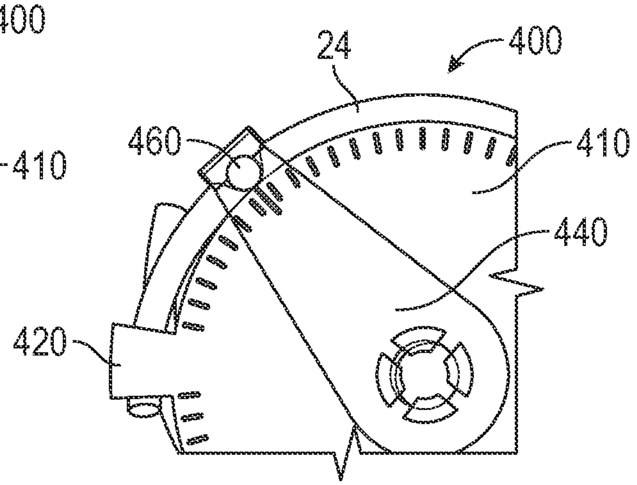
FIG. 25 depicts a perspective view of a stable flow regulator assembly coupled to an IV tube, according to aspects of the disclosure.

In aspects of the disclosure, as shown in FIG. 25, the stable flow regulator assembly 400 may include a movable roller 460 that may be coupled to the tube arm 440 in place of the press member 445. For example, the movable roller 460 may be configured to spin around within the tube arm 440 (e.g., on a shaft between opposing arm segments 446*a*, 446*b*). Here, the movable roller 460 may compress the tube 24 with a similar force factor as conventional roller clamps, for example.

Figure 26:
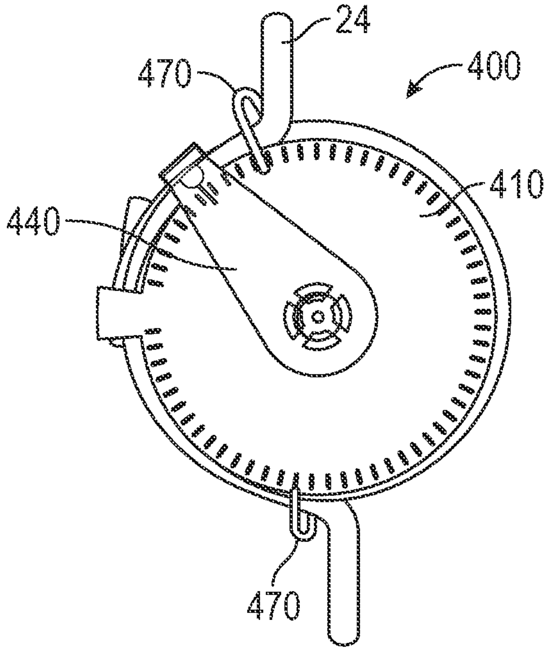
FIG. 26 depicts a perspective view of a stable flow regulator assembly coupled to an IV tube, according to aspects of the disclosure.

In aspects of the disclosure, as shown in FIG. 26, the stable flow regulator assembly 400 may include securing members 470 (e.g., hooks) disposed at portions of the perimeter 412 to align the remaining tube portions as desired. For example, two securing members 470 may be coupled at opposing ends of the body 410 to align the incoming and outgoing tubing 24 with the shaft hole 416. As another example, the securing members 470 may be used to hold the tube 24 against only a portion of the perimeter 412 of the body 410 (e.g., 90 degrees, 270 degrees). Here, the radial tube groove 430 may be configured as previously shown, or it may be shortened to match the portion of the tube bearing perimeter 412.

Figure 28:
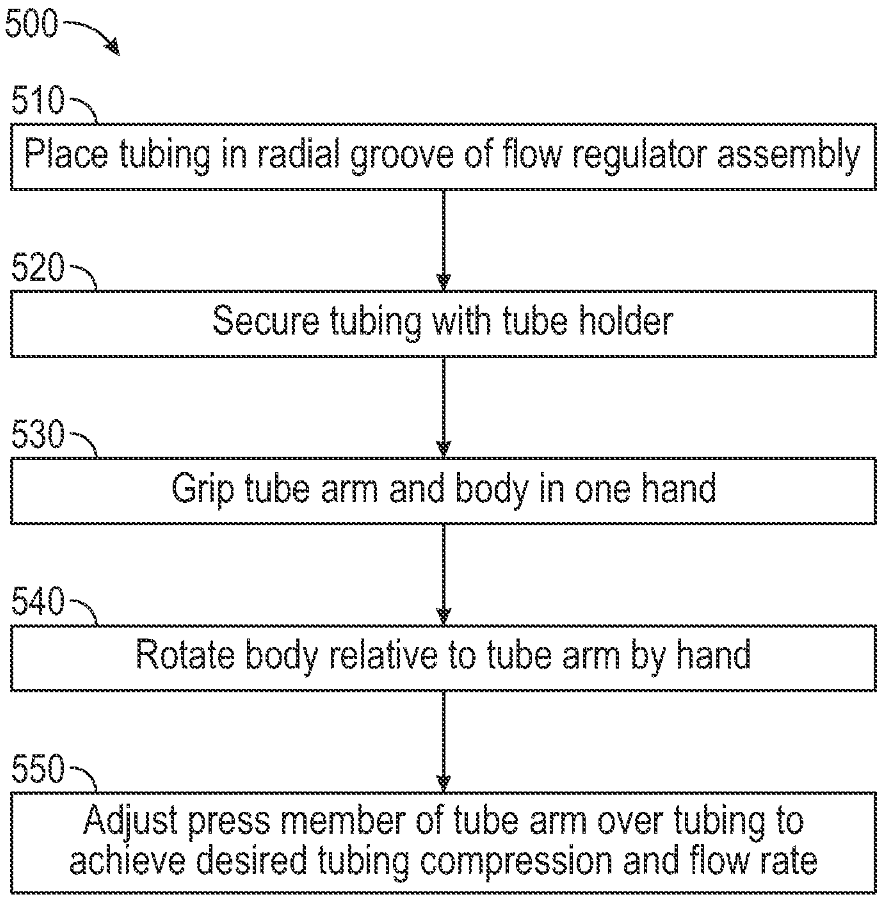
FIG. 28 illustrates a method of operating a stable flow regulator assembly, according to aspects of the disclosure.

With reference to FIG. 28, a method 500 of operating a stable flow regulator assembly (e.g., stable flow regulator assembly 400) is provided. In step 510, tubing (e.g., IV tube 24) is placed or inserted into a body (e.g., body 410) such that the tubing is disposed within a radial tube groove (e.g., radial tube groove 430). The tubing is further secured by a tube holder (e.g., tube holder 420) and disposed under a press member (e.g., press member 445) of a tube arm (e.g., tube arm 440) that is rotationally coupled to the body, in step 520.

In step 530, as shown in FIG. 27, the stable flow regulator assembly is gripped by hand such that the tube arms are gripped on both sides of the body (e.g., by a thumb and a middle finger of one hand) and the body is engaged by another finger (e.g., index finger of the same hand). The body is rotated by hand (e.g., by turning the body relative to the tube arm), in step 540.

In step 550, the press member position relative to the tube in the radial tube groove is adjusted to cause the desired flow rate by rotating the body relative to the tube arm until the depth of the radial tube groove compresses the tubing a suitable amount to achieve the desired flow rate. For example, regarding stable flow regulator assembly 400, as the body 410 is turned relative to the tube arm 440, the depth of the radial tube groove 430 decrease or increases, depending upon which way the body 410 is turned, causing the tube 24 within the radial tube groove 430 to be compressed more or less, respectively.

In aspects of the disclosure, the stable flow regulator assembly 100, 200, 400 provides that the angle between the normal of spiral and the circle (e.g., perimeter of body 110, 210, 410) is very small (e.g., less than 5 degrees). In aspects of the disclosure, the outward biasing force from the compressed tube 24 is radial, thus no tangential force is exerted on the tube arm 140, 240, 440 by the outward biasing force, thus preventing or minimizing drift of the tube arm 140, 240, 440 along the perimeter of the body 110, 210, 410 due to the outward biasing force. Accordingly, in order to rotate the tube arm 140, 240, 440, an external tangential force must be provided (e.g., by manual force from a finger). In aspects of the disclosure, a positive locking feature is provided by the interaction between the holding members 114, 414 and the arm holding members 149, 449. This interaction also provides sound feedback (e.g., clicking sounds) when the tube arm 140, 240, 440 is rotated.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure, element or feature relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A stable flow regulator assembly comprising:

a body comprising:

a tube slot disposed adjacent a perimeter of the body, the tube slot having an opening at the perimeter to slidingly receive a portion of an intravenous (IV) tube; and a spiral slide groove extending into the body from the tube slot, wherein a width of the spiral slide groove narrows as the spiral slide groove extends further into the body; and a tube arm rotatingly coupled to the body, the tube arm having a slot open to the perimeter of the body and configured to slidingly receive the IV tube when the slot is aligned with the tube slot of the body, wherein the stable flow regulator assembly is configured to regulate a flow rate of fluid flowing through the IV tube based on an amount of compression of the IV tube due to a position of the IV tube within the spiral slide groove.

2. The stable flow regulator assembly of claim 1, wherein the tube arm comprises a shaft rotatingly coupled through a shaft hole of the body.

3. The stable flow regulator assembly of claim 2, wherein the shaft includes a snap member configured to compress when the shaft is fed through the shaft hole and to expand when the snap member exits the shaft hole on an opposing side of the body.

4. The stable flow regulator assembly of claim 3, wherein the tube arm comprises opposing arm segments coupled together by hinge members, wherein the shaft and the snap member are disposed on a first arm segment of the opposing arm segments and a receiving hole is disposed on a second arm segment of the opposing arm segments, wherein the second arm segment is configured to fold over the perimeter of the body via the hinge members and the snap member is disposed through the receiving hole.

5. The stable flow regulator assembly of claim 4, wherein the first arm segment and the second arm segment and the hinge members collectively have two side portions that define the slot in the tube arm.

6. The stable flow regulator assembly of claim 1, further comprising a plurality of holding members disposed on a surface of at least one side of the body, the plurality of holding members spaced along a portion of the spiral slide groove.

7. The stable flow regulator assembly of claim 6, wherein the tube arm includes one or more arm holding members configured to slidingly engage with the plurality of holding members on the body.

8. The stable flow regulator assembly of claim 1, further comprising a plurality of indicator markings disposed on a surface of at least one side of the body, the plurality of indicator markings spaced along one of a portion of the spiral slide groove and the perimeter of the body.

9. The stable flow regulator assembly of claim 1, wherein the spiral slide groove has a widest width of 4 mm and a narrowest width of 0.15 mm.

10. The stable flow regulator assembly of claim 1, further comprising at least one flap extending from the body into the tube slot, the at least one flap configured to flex inward to allow slidable sideways movement of the IV tube into the tube slot and to flex back to a default position to prevent slidable sideways movement of the IV tube back out of the body.

11. The stable flow regulator assembly of claim 1, further comprising a locking member coupled to the body and movably disposed over the tube slot, wherein the locking member is clear of the tube slot in a first position for slidable passage of the IV tube into the tube slot, and wherein the locking member is positioned to block slidable passage of the IV tube out of the body in a second position.

12. The stable flow regulator assembly of claim 1, further comprising a grip disposed on the perimeter of the body, the grip comprising a plurality of projections extending radially outward from the body.

13. The stable flow regulator assembly of claim 1, further comprising a plurality of ratchet teeth disposed on a surface of at least one side of the body, the plurality of ratchet teeth spaced around a portion of the spiral slide groove and configured for a ratchet engagement with the tube arm.

14. The stable flow regulator assembly of claim 1, further comprising a plurality of flaps disposed on a surface of at least one side of the body, the plurality of flaps spaced around the perimeter of the body and extending outward past the perimeter of the body.

15. The stable flow regulator assembly of claim 1, further comprising one or more flaps disposed on the tube arm.

16. A method of operating the stable flow regulator assembly of claim 1, the method comprising:

inserting an intravenous (IV) tube into the slot on the tube arm that is rotatingly coupled to the body;

inserting the IV tube into the spiral slide groove disposed within the body of the stable flow regulator assembly wherein the inserted IV tube is uncompressed by side walls of the spiral slide groove;

rotating the tube arm relative to the body to slide the IV tube along varying widths of the spiral slide groove; and ceasing rotating the tube arm relative to the body when the IV tube is positioned within a particular width of the spiral slide groove for which a resulting compression of the IV tube corresponds to a particular fluid flow rate through the IV tube.

* * * * *